United States Patent [19]

Ray

[11] Patent Number: 4,599,169
[45] Date of Patent: Jul. 8, 1986

[54] HEATING AND COOLING APPARATUS FOR CHROMATOGRAPHY COLUMN

[75] Inventor: Curtis Ray, Benicia, Calif.

[73] Assignee: Varian Associates, Inc., Palo Alto, Calif.

[21] Appl. No.: 584,421

[22] Filed: Feb. 28, 1984

[51] Int. Cl.⁴ ............................................. G01D 15/08
[52] U.S. Cl. ..................................... 210/175; 55/197; 55/386; 210/198.2
[58] Field of Search .................... 55/197, 386, 208; 210/198.2, 149, 175

[56] References Cited

U.S. PATENT DOCUMENTS

| | | | |
|---|---|---|---|
| 4,038,055 | 7/1977 | Varano | 55/197 |
| 4,070,169 | 1/1978 | Iwao et al. | 55/267 |
| 4,111,643 | 9/1978 | Welland | 432/48 |
| 4,181,613 | 1/1980 | Welsh et al. | 210/179 |

*Primary Examiner*—John Adee
*Attorney, Agent, or Firm*—Stanley Z. Cole; Allan M. Lowe; David Schnapf

[57] ABSTRACT

A baffle divides a housing into first and second compartments. The first compartment includes a chromatography oven having a fan for circulating heated air over the columns while the oven is closed and for sucking ambient temperature cooling air in the first compartment into the oven while the oven is open. Ambient air is sucked into a tortuous path in the first compartment. Cooling air from the second compartment flows into the first compartment via openings in the baffle. The cooling air flows over the oven exterior and is at least partially sucked into the oven by an oven fan while the oven is open. The oven heater, coaxial with the blades, is located between an oven wall and blades. A ring baffle, having approximately the same diameter as and coaxial with the blades, is located between the wall and the blades. A fan outside of the oven sucks air from the oven through an outlet while the oven is open. The second fan is separated from an inlet for the oven by a baffle having an opening through which air is sucked by the second fan while the oven is closed. The second compartment includes a casing for fluid flow controllers for the columns, which casing is maintained at constant temperature by ambient air sucked around the second compartment.

30 Claims, 4 Drawing Figures

HEATING AND COOLING APPARATUS FOR CHROMATOGRAPHY COLUMN

TECHNICAL FIELD

The present invention relates generally to chromatography apparatus and more particularly to an apparatus for heating and cooling chromatography columns.

BACKGROUND ART

Prior art apparatus for heating and cooling chromatography columns employ ovens having insulated walls containing brackets on which chromatography columns are mounted. Conduits mounted on the holders supply and remove chromatography carriers and samples from the columns. Air in an oven is electrically heated and circulated by fans so that the heated air is directed to be incident on the columns, to heat the carriers and samples in the columns to an adequate temperature. To provide the required temperature for the carriers and samples in the column, the air frequently must be heated to 400° C. to 500° C.

When a chromatography operation has been completed it is desired to cool the columns as quickly as possible, as is typically done by introducing ambient outside room temperature air into the oven interior. In one prior art configuration, the ambient air is circulated away from the fan blades so it contacts plural baffles and walls inside of the oven and is then drawn back in through the fan by the fan blades.

While the prior art structure is generally satisfactory, there are certain disadvantages associated with it. Because the oven interior walls and baffles have a relatively large thermal inertia and mass, the ambient, cooling air introduced into the oven interior after the column is no longer operating is heated by these surfaces. This has a tendency to increase the time required to cool the oven interior and prolong the time between adjacent tests. Also, during the column operating mode, while the oven is closed and heating the columns, the air circulated by the fan contacts the oven interior walls and baffles, to transfer heat to these surfaces. This transfer of heat to the baffles and interior oven surfaces increases the temperature gradient within the oven. It is desirable to minimize temperature gradients within the oven during the heating operation so as to maintain the temperature of the chromatography columns constant.

In one prior art configuration, the air passes over the heater downstream of the mixing fan. In such an arrangement full advantage of the mixing action provided by the fan does not occur. In other configurations, the baffles and oven interior walls direct the air back to the fan inlet without the air ever being incident on the columns. Thus, this air adds to the thermal inertia of the oven, to increase the length of time required for cooling.

A problem with the prior art ovens is that during cooling the hot air can not be removed from the oven by exhaust fans located in proximity to the oven outlet. This is because the air to be removed from the oven during the cooling operation is so hot that it damages bearings of the fan. Therefore, it is desired to lower the thermal mass of the oven to as great as extent as possible so air removed from the oven during initial stages of the cooling operation has sufficient heat to damage fan components in close proximity to the outlet.

It is customary for chromatography column apparatus to include controllers, such as valves, for the flow of carrier and sample fluids into and out of the columns. The flow controllers are usually temperature sensitive, whereby it is desired to maintain the temperature of the flow controllers and a compartment or housing in which they are located substantially constant. It is also desired to locate the flow controller compartment and the oven in a single housing for the entire chromatography unit.

It is, accordingly, an object of the present invention to provide a new and improved chromatography column apparatus.

A further object of the invention is to provide a new and improved apparatus for heating and quickly cooling chromatography columns.

A further object of the invention is to provide a new and improved chromatography column heating and cooling apparatus wherein air directed from a heater in an oven toward the columns is incident on the columns prior to being incident on any interior baffles or walls of the oven.

A further object of the invention is to provide a new and improved chromatography column oven having low thermal mass so that heated air in the oven is quickly cooled.

Still a further object of the invention is to provide a chromatography column oven that can be quickly reused after an operating cycle has been completed.

A further object of the invention is to provide a new and improved gas chromatography column oven having a fan associated therewith, wherein the fan is positioned to suck air out of the oven.

A further object of the invention is to provide a new and improved chromatography column housing wherein the chromatography column oven and a container for flow control devices for the chromatography columns are cooled and maintained at relatively constant temperature by ambient outside air while the columns are in operation.

DISCLOSURE OF INVENTION

In accordance with one aspect of the invention, an oven for heating chromatography columns mounted in the oven and for enabling the columns mounted in the oven to be cooled relatively quickly comprises an oven enclosure having a wall and an interior containing mounting means for the columns. Axial fan blades, a heater and a baffle inside of the oven are centrally mounted with respect to the oven wall. The baffle and heater are located between the wall and the blades, with the baffle surrounding the heater. The baffle, heater and blades are configured and located in the oven enclosure so that the axial fan is transformed into a mixed tangential and axial fan so that air directed by the blades is incident on the columns prior to being intercepted by walls of the oven.

On the wall are located selectively opened and closed air inlet and outlet means. When the inlet and outlet means are open, the position thereof is such that cooling air at approximately room temperature and pressure (ambient temperature and pressure) is drawn by the blades through the inlet means and the baffle into the oven enclosure to cool the columns. The baffle and fan are such that the cooling air drawn into the enclosure by the blades through the inlet means can not flow directly to the outlet means. The inlet, outlet, baffle and fan are positioned and configured such that the outlet is at a high pressure region in the enclosure to assist in rapid removal of hot air from the enclosure.

In the preferred embodiment, the only elements in the interior of the oven are the fan blades, a shaft carrying the blades, the baffle, the heater and the column mounting means, which includes conduits for fluids and samples flowing into and out of the columns. The small number and mass of the components in the enclosure causes the enclosure to have a relatively low thermal mass.

In a preferred embodiment, the baffle is configured as a ring having a wall parallel to the axis. The ring and blades have approximately the same diameter to assist in providing the desired flow pattern within the oven interior.

When the oven is closed and the columns are being operated at a high temperature, the fan operates in a mixed flow mode, whereby the column heating air exiting the fan blades has a substantial tangential velocity, a medium axial velocity and a minimal radial velocity. Most of the air, after passing over the columns, is sucked axially by and into the front of the blades. A relatively small amount of the air that has passed over the columns is sucked by and through the rear of the blades, by way of clearances between the blades and the exterior wall. The air sucked into the rear of the blades flows in a swirling pattern through the baffle where it has a tendency to be confined for a relatively long interval in proximity with the heater coil from which it acquires a significant amount of heat. The hot air in the baffle mixes with the air sucked into the front of the blades. The resulting mixture, having a relatively high temperature of 400° C.–500° C., exits the fan blades with the stated velocity relationship.

To assist in removing air quickly from the oven interior during cooling, blades of a further fan, located outside of the oven, suck air through the outlet means while the outlet means is open. Because of the low thermal mass of the interior of the oven, the air sucked by the further fan has insufficient heat to damage the further fan.

The further fan is located in a low pressure cavity separated from the inlet means by a further baffle. The further baffle has an opening so air is sucked through the opening into the low pressure cavity by the further fan while the inlet and outlet means are closed.

In accordance with a further aspect of the invention, the chromatography column and a closed compartment for fluid flow controllers for the columns are located in a common housing that is divided by an additional baffle into first and second compartments. The first compartment includes the oven in which the chromatography columns are mounted, as well as the blades of a further fan, outside of the oven. The first compartment includes a tortuous path having first opening means through which ambient cooling air is sucked. The baffle has second opening means through which cooling air from the second compartment flows into the first compartment. The cooling air flowing through the first and second opening means flows over the oven exterior to maintain it at a relatively constant cool temperature. The cooling air flowing through the first and second opening means is at least partially sucked into the oven by the blades inside the oven while the oven is open.

The second compartment, in addition to including the closed compartment for the fluid flow controllers, has a third opening means leading to ambient air outside of the housing. The ambient cooling air drawn through the third opening means flows about the closed compartment to have a substantial effect on the closed compartment temperature to maintain the closed compartment at a substantially constant temperature. The ambient cooling air drawn through the third opening means also flows through the second opening means into the first compartment.

The above and still further objects, features and advantages of the present invention will become apparent upon consideration of the following detailed description of one specific embodiment thereof, especially when taken in conjunction with the accompanying drawings.

BEST MODE FOR CARRYING OUT THE INVENTION

Figure 1:
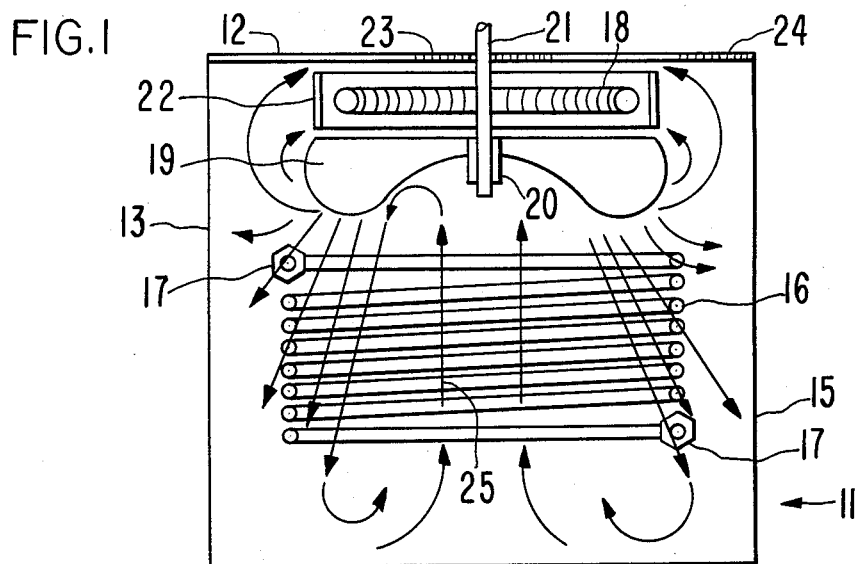
FIG. 1 is a schematic top view of an oven in accordance with the present invention, during an operating cycle of chromatography columns, i.e., while the columns are being heated.

Reference is now made to FIG. 1 of the drawing, a schematic top view of chromatography oven 11 in accordance with a preferred embodiment of the invention. Oven 11 is shaped as a right parallelepiped having metal walls 12–15; wall 14 is actually an access door to the interior of the oven. On the interior of each of the walls of oven 11 is an appropriate amount of thermal insulation (not shown). Chromatography columns 16 are held in situ by mounting brackets 17 which extend through the roof of oven 11. Columns 16 and brackets 17 are of conventional design, with the brackets being provided with conduits for enabling carrier and sample fluids to be supplied to and withdrawn from columns 16 in a conventional manner.

Mounted in close proximity to wall 12, and fixedly connected to wall 12 is electric coil heater 18, having a ring like shape, as disclosed, for example, in Iwao et al, U.S. Pat. No. 4,070,169. Heater 18 is connected to wall 12 by brackets (not shown). Heater 18 is supplied with sufficient current to enable the temperature of air in oven 11 to be in the range of 400°–500° C.

Axial fan blades 19 circulate the heat generated by heater 18. Fan blades 19 are carried by shaft 21 which extends through the geometric center of wall 12 from an electric motor (not shown) mounted outside of oven 11. Blades 19 are coaxially and symmetrically mounted on shaft 21 so that the center of blades 19 is on a line perpendicular to wall 12 and which intersects the center of wall 12. Blades 19 are of a type whereby in an unrestricted, free air environment, there is axial flow induced by the blades into the blades as they rotate. In the unrestricted, free air mode, there are substantially no circular or radial flows induced by blades 19.

Ring baffle 22 assists in controlling the flow of hot air in oven 11. Baffle 22 and heater 18 are concentric with shaft 21, with the baffle and heater being positioned between blades 19 and wall 12. Ring 22 has a diameter approximately equal to the diameter of blades 19 and a wall which extends axially of shaft 21 and blades 19. Ring 22 surrounds heater 18 and has an axial extent greater than that of the heater.

Blades 19 and baffle 22 are positioned in oven 11 in such a manner as to modify the free air flow pattern of blades 19 so the flow pattern is a mixed axial and circular mode. While oven 11 is closed and heater 11 is activated, air in oven 11 is sucked axially into blades 19 substantially from the front center of the blades, i.e., in the direction indicated by arrows 25. Additional air is sucked by blades 19 from the back of the blades through the interior of baffle 22 by way of the clearances between wall 12 and baffle 22 and the clearance between the edge of the blades and baffle 22. The air sucked into the back of blades 19 through baffle 22 has a swirling, circular pattern, and thereby flows over heater coil 18 so that there is a substantial amount of heat transfer between the air in the interior of baffle 22 and heater coil 18. The air flowing into the front and back of blades 19 is mixed and directed by blades 19 toward columns 16 so that the air exiting blades 19 intercepts columns 16 prior to being incident on any walls of oven 11. The air exiting blades 19 has a substantial tangential (i.e., circular) velocity, a medium axial velocity, but a minimal radial velocity. Because air directed by fan 19 intercepts columns 16 prior to contacting any walls of oven 11, the air incident on the columns has a uniform temperature and is not cooled by the walls. Because columns 16 are uniformly heated by the hot air incident thereon, uniform and optimum performance of the columns are attained.

The only elements inside of oven 11 are therefore columns 16, brackets 17, blades 19, shaft 21, baffle 22 and heater 18. Because of the small number of elements inside of oven 11, the oven interior has a low thermal mass and thereby can be cooled very quickly in response to ambient air.

To cool the interior of oven 11, wall 12 includes inlet door 23 and outlet door 24. Doors 23 and 24 are simultaneously opened and closed during the cooling and heated operations, respectively, by an electric motor (not shown) mounted outside of oven 11. Inlet door 23 is mounted on wall 12 substantially equidistant between walls 13 and 15, above shaft 21. Outlet door 24 is between the outer periphery of ring baffle 22 and wall 15, a high pressure point in oven 11, to augment air flow from the interior of oven 11 to outside of the oven.

During cooling, while doors 23 and 24 are open, cool ambient, room temperature and pressure air is sucked by blades 19 through door 23 and inside of baffle 22. At this time, heater 18 is deenergized and the temperature of cool air flowing through baffle 22 is not affected by heater 18. The pressure in the region of oven 11 adjacent wall 12 and outside of baffle 22 is relatively high because this region of the oven interior is isolated to a large extent by baffle 22 from the low pressure area at the inlet of blades 19 and because blades 19 provide a tangential flow of air in oven 11 about the periphery of baffle 22 into this region. The tangentially flowing air decreases in speed as it approaches the corner of oven 11 where door 24 is located to provide the high pressure region.

The high pressure flow of air in oven 11 to outlet door 24 augments suction action established by an axial fan 62 (shown in FIG. 2) downstream of door 24, outside of the oven. Because of the low thermal mass of the components in oven 11, the air flowing through outlet 24 quickly drops to a temperature which is sufficiently low to prevent damage to the axial fan outside of oven 11.

Figure 2:
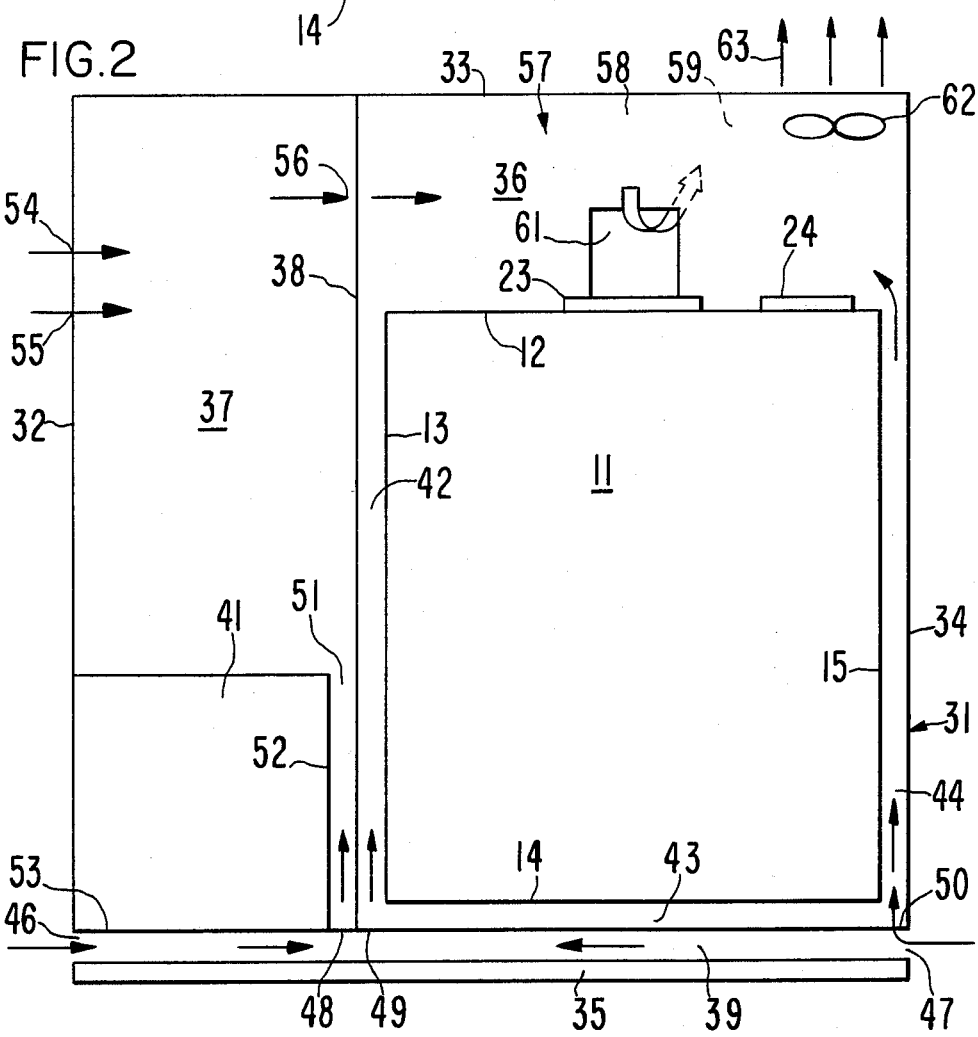
FIG. 2 is a schematic top view of a housing, in accordance with the invention, wherein the housing contains a chromatography oven and a container for temperature sensitive flow control components, and the oven is heating the columns.
Figure 3:
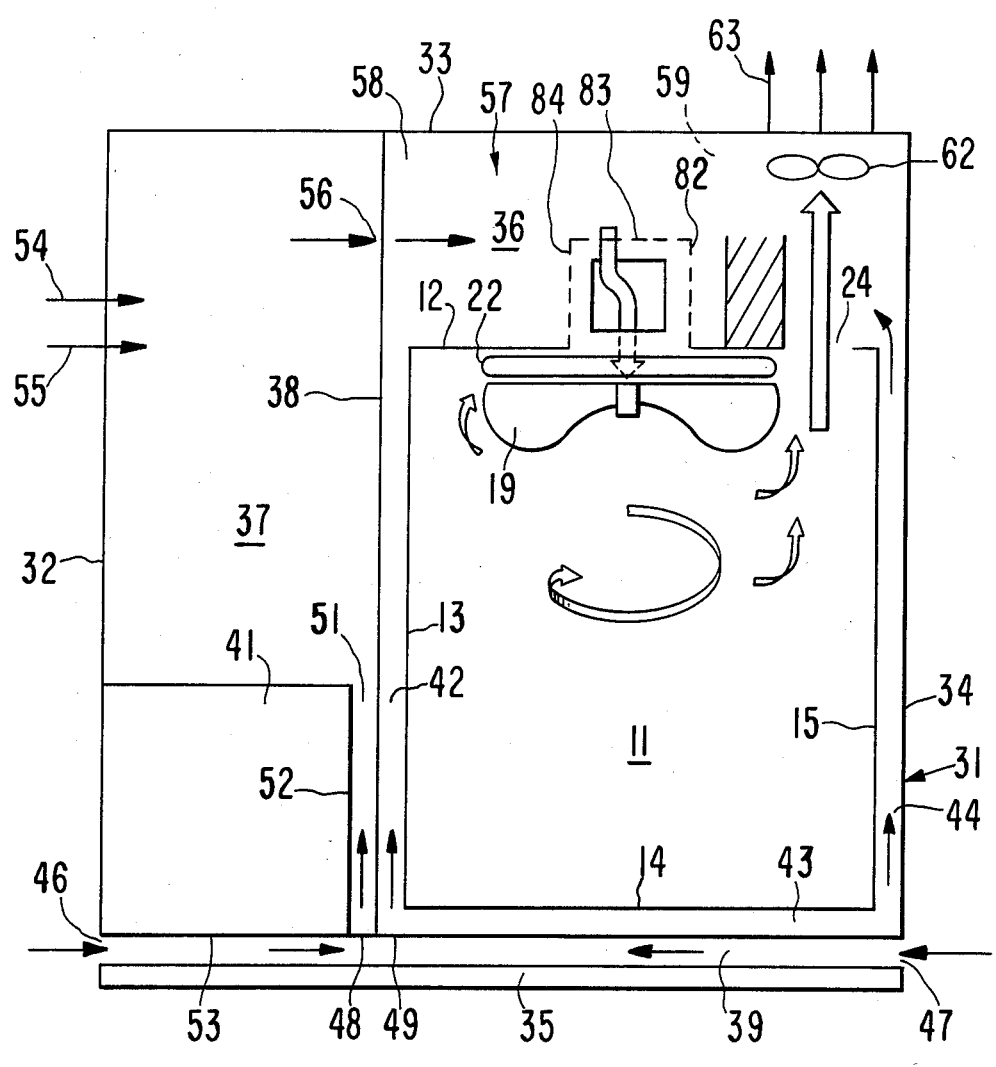
FIG. 3 is a schematic view of the apparatus illustrated in FIG. 2 during a cooling cycle of the columns.

Oven 11 is located in housing 31, as illustrated in the schematic top views of FIGS. 2 and 3. Housing 31 is formed as a right parallelepiped having walls 32, 33 and 34 and door 35. Housing 31 is divided into first and second compartments 36 and 37 by baffle 38 which extends parallel to walls 32 and 34 between passage 39 just behind door 35 and wall 33. Compartment 36 contains oven 11, while compartment 37 contains housing 41 for fluid flow control elements, such as solenoid controlled valves and electronically controlled circuits therefore. The valves control the flow of carrier fluids and samples into columns 16 via conduits (not shown) which extend between housing 41 and brackets 17 in oven 11.

The exterior surfaces of oven 11 and housing 41 are maintained at a relatively constant temperature, approximately equal to the temperature of ambient air around the periphery of housing 31. Thereby, temperature sensitive elements in housing 41 are maintained at a substantially constant temperature. Also a relatively constant temperature is maintained around the periphery of oven 11 to assist in preventing different regions of the oven from having a substantial temperature gradient between them so columns 16 operate in a uniform manner. Maintaining the periphery of oven 11 at a relatively constant, relatively cool ambient temperature facilitates rapid cooling of the interior of the oven during a cooling cycle.

Figure 4:
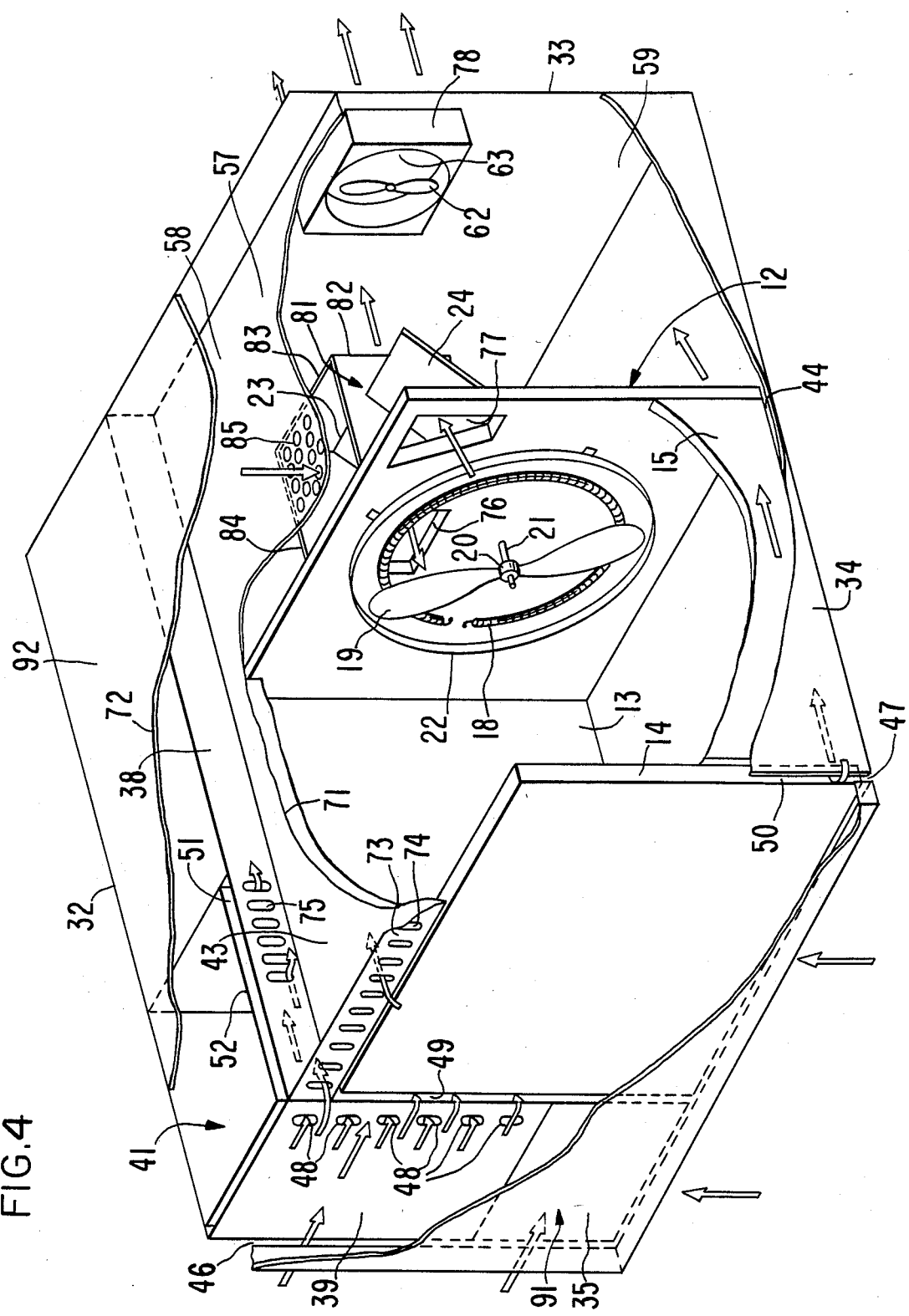
FIG. 4 is a perspective view of a chromatography apparatus in accordance with the invention.

To maintain the exterior walls of oven 11 at an ambient temperature, a tortuous path for ambient air is established around the peripheral walls of the oven. The tortuous path includes a portion of passage 39, as well as narrow passages 42, 43 and 44. Passage 43 is illustrated schematically in FIGS. 2 and 3 as being between wall 14 and passage 39; however in the preferred embodiment, as illustrated in FIG. 4, passage 39 extends between wall 14 and door 35 and passage 43 comprises passages between the ceiling of oven 11 and the roof of housing 31. Passage 42 extends completely along the length of oven wall 13 and along a major portion of baffle 38. Passage 44 extends throughout the length of wall 15 and along the majority of wall 34. Passages 39, 42, and 44 are relatively long and narrow and have flow impedances substantially equal to the flow impedance of the separation of oven 11 from the top face thereof, i.e., at right angles to the plane of the sheet containing FIG. 2. Passage 43 has a similar flow impedance.

Air flows into opposite ends of passage 39 by way of openings 46 and 47 in walls 32 and 34, respectively. Openings 46 and 47 extend almost completely between the base and roof of housing 31. Air flowing into passage 39 from openings 46 and 47 flows through openings 48, 49 and 50 into passages 51, 42 and 44, respectively. Passage 44 has a relatively high flow impedance because it has a narrow width and long length, so that only a small portion of the air flowing through opening 47 flows into passage 44. Passage 51 subsists between baffle 38 and wall 52 of housing 41; wall 52 lies parallel to housing wall 32 which forms an exterior wall of housing 41 to assist in maintaining the exterior and interior of housing 41 at a uniform temperature. Opening 48 is thus positioned between wall 52 and baffle 38, while opening 49 is located between wall 13 and baffle 38. Opening 48 extends downwardly from the ceiling of housing 31 to the bottom of housing 41, having a height approximately equal to one-half of the height of housing 31. Opening 49 extends almost from the roof to the base of housing 31, through a distance substantially equal to the height of oven 11. Because the portion of passage 39 between openings 46 and 48 is along wall 53 of housing 41 and because passage 51 extends throughout the length of wall 52, two sides of housing 41 are directly cooled by ambient air introduced into passage 39, while the side wall of housing 41 opposite to wall 52 and the ceiling of housing 41 are in direct contact with ambient air.

The exterior walls of oven 11 are cooled by the ambient air flowing through openings 49 and 50 into passages 42 and 44, as well as similarly dimensioned passages above the ceiling of oven 11. Relatively long narrow passages 39, 42, 43, 44 and 51 have a high thermal inertia so that the air located therein has a tendency to remain at constant temperature.

Ambient air is also introduced into compartment 37 through openings 54 and 55 (shown as arrows in FIGS. 2 and 3). Openings 54 and 55 are first and second sets of slots which extend vertically between the base of housing 31 and a plane containing the bottom of housing 41. Openings 54 and 55 extend between wall 33 and the projection of a line from oven wall 12 to wall 32.

Air in compartment 37 flows through slotted openings 56 (shown as arrows in FIGS. 2 and 3) into compartment 36. Slotted openings 56 extend between the ceiling and floor of housing 31 and are located approximately half way between oven wall 12 and housing wall 33. Thereby, air flows into the portion of compartment 36 between oven wall 12 and housing wall 33 by way of passages 42 and 44, as well as slotted openings 56 in baffle 38.

The portion of compartment 36 between walls 12 and 33 is divided by baffle 57 into first and second segments 58 and 59. Baffle 57 includes aperture 61 between segments 58 and 59. Walls 82–84 of cavity 81 in segment 59 separates inlet and outlet doors 23 and 24; cavity 81 includes aperture 61 to provide direct air flow communication with door 23. Located immediately downstream of outlet door 24 in segment 59 are axial fan blades 62, whereby segment 59 can be considered as a low pressure chamber. Low pressure chamber 59 includes circular opening 63 (indicated by arrows in FIGS. 2 and 3), which is located immediately downstream of blades 62 and has a diameter slightly greater than that of the blades. Blades 62 and opening 63 have an area approximately equal to the opening in wall 12 covered by door 24 and are positioned immediately downstream of the outlet opening so that air drawn by the blades from oven 11 easily escapes into the atmosphere outside of housing 31.

With oven 11 in operation and doors 23 and 24 closed, as illustrated in FIG. 2, fan 62 sucks air through openings 46, 47, 54 and 55 into the interior of housing 31. The air sucked into openings 46 and 47 flows into passage 44 and down passage 39 to openings 48 and 49, thence into passages 42 and 51, as well as into passages 43 above oven 11. The air flowing in passage 51 combines with the air flowing through openings 54 and 55 and is sucked into compartment 36 through openings 56. The air flowing through openings 56 combines in segment 59 with the air flowing through passages 42 and 44. The air has approximately atmospheric temperature and pressure when it reaches opening 61. The air at opening 61 is sucked into low pressure chamber 59 by fan 62, thence is forced out of chamber 31 via opening 63.

During a cooling cycle, while inlet and outlet doors 23 and 24 are open, the flow into chambers 36 and 37 is the same as described supra with regard to the heating cycle. However, during the cooling cycle, a significant portion of the air which flows through aperture 61 is sucked by blades 19 through inlet door 23, as illustrated in FIG. 3. Thereby, the air entering the interior of oven 11 is at approximate atmospheric temperature and pressure. Blades 19 suck the air flowing through door 23 axially through the interior of baffle to and establish a circular air flow inside of oven 11. Because of the low thermal mass in the interior of oven 11, the circularly rotating air sucked into the oven by blades 19 quickly reduces the temperature of the components in the interior of the oven. After the air sucked by blades 19 into the interior of oven 11 has made at least three quarters of a turn in the oven, it reaches the high pressure region in the oven between the exterior of baffle 22 and wall 15, adjacent opening 24. A significant portion of the air adjacent door 24 is sucked through door 24 by fan blades 62 and is evacuated from housing 31 through opening 63. The air flowing through door 24 mixes with other room temperature air in segment 52 which is not sucked into oven 11 by blades 19. Mixing of the hot air escaping through door 24 with the ambient temperature cooling air assists in preventing the flow of very hot, possibly destructive air across a bearing (not shown in FIGS. 2 and 3) between fan blades 62 and a drive shaft therefor.

Reference is now made to FIG. 4 of the drawing, a perspective, cut-away view of oven 11 and housing 31. The components schematically illustrated in FIGS. 1–3 are illustrated in FIG. 4 in the actual spatial location thereof as employed in a preferred embodiment of the invention.

As illustrated in FIG. 4, ceiling 71 of oven 11 is displaced from roof 72 of housing 31 to form passage 43 in segment 58, both schematically illustrated in FIGS. 2 and 3. Slotted baffle plate 73 projects above oven access door or wall 14, so that the slots in plate 73 enable cool air to flow from passage 39 over ceiling 71 of oven 11. Air flow over ceiling 71 is also by way of passage 51, via slots 75 at the top of baffle 38, between ceiling 71 and roof 72.

In FIG. 4, wall 12 includes rectangular inlet opening 76, centrally positioned on wall 12 above fan blade shaft 21. Outlet opening 77, in the upper right hand corner of wall 12 outside of baffle 22, is shaped as a trapezoid having a base extending vertically and parallel to the edge of wall 12 and a hypotenuse extending upwardly toward the center of wall 12. Thereby, opening 77 has an area which is close to maximizing the area between the exterior of baffle 22 and the upper and side edges of wall 12 in the high pressure region in oven 11 adjacent wall 12. The trapezoidal configuration for opening 77 enables the opening to be more easily stamped than if the portion of the opening adjacent baffle 22 were a curve, the optimum configuration for the portion of the opening adjacent the baffle.

Fan blades 62 are located so that the axis thereof is coincident with the center of opening 77. Fan blades 62 have a diameter approximately equal to the vertical extent of opening 67. The blades of fan 62 are located in shroud 78, to assure axial flow of air into the fan.

Inlet door 23 is located in cavity 81, defined by vertically extending rectangular walls 82–84 which are at right angles to each other. Walls 82 and 84 abut against the exterior of wall 12 and are connected to each other by wall 83. Cool air flows into cavity 81 by way of a rectanglar matrix 85 of openings in ceiling 71; matrix 85 is in the portion of ceiling 71 that extends between walls 12 and 33. The apertures in matrix 85 cover an area in ceiling 71 that is coextensive with the area of cavity 81 between walls 12, 82, 83 and 84. The bottom of cavity 81 is open so that when inlet door 23 is closed, all of the air sucked into cavity 81 by way of the apertures in matrix 85 is drawn through the open bottom of cavity 81 by fan blades 62. When, however, door 23 is open, the top edge of the door abuts against wall 83 and the vast majority of the air flowing through the apertures in matrix 85 is sucked by blades 19 into oven 11 to provide cooling. There is some leakage of air flowing through the apertures in matrix 85 around the edges of open door 23 by virtue of the suction action of fan blades 62. Thus, the portion of ceiling 71 between walls 12 and 33 functions as baffle 36, while the inlet into cavity 81 by way of the apertures in matrix 85 and the open bottom of the cavity function functions as aperture 61. Wall 83 is spaced from wall 33 so that fan blades 62 draw air through slots 56 (shown in FIGS. 2 and 3) at all times while fan blades 62 are turning.

Not illustrated in FIG. 4 is the electric motor for driving shaft 21, which motor is mounted on the exterior of wall 12, immediately below the opening at the bottom of cavity 12. Thereby, cool air flows over the electric motor driving blades 19 to provide optimum operation thereof. An electric motor (not shown) for driving the fan blades 62 is mounted outside of housing 31 on wall 33.

To complete the description of housing 31 and compartment 37, an electrically driven plotter 91 is mounted directly beneath flow controller housing 41. Electronic components are mounted on printed circuit cards in compartment 92, between controller 41 and wall 33, as well as between wall 32 and baffle 38.

While there has been described and illustrated one specific embodiment of the invention, it will be clear that variations in the details of the embodiment specifically illustrated and described may be made without departing from the true spirit and scope of the invention as defined in the appended claims.

I claim:

1. An oven for heating chromatography columns mounted therein and for enabling the columns mounted in the oven to be cooled relatively quickly comprising an oven enclosure having a wall, the oven having an interior in which is located: mounting means for the columns, a fan assembly having a shaft carrying blades centrally mounted with respect to the wall, the shaft extending through the wall geometric center and connected to be driven by a motor outside of the enclosure, a heater located coaxially with the shaft between the wall and the blades, a baffle surrounding the heater located coaxial with the shaft between the exterior wall and blades, the baffle, heater and blades being configured and located in the enclosure so that the fan functions as a mixture circumferential and axial fan whereby air directed by the blades is incident on the columns without first being intercepted by walls of the oven and the circumferentially directed air is substantially prevented by the baffle from directly reaching the heater, whereby the small number and mass of items in the enclosure causes the enclosure to have a relatively low thermal mass; and selectively opened and closed air inlet and outlet means on the wall, the inlet and outlet means being located so that when the inlet and outlet means are open, air at approximately ambient temperature and pressure is drawn by the blades through the inlet means and the baffle into the enclosure to cool the columns and air drawn into the enclosure by the blades through the inlet means does not flow directly to the outlet means.

2. The oven of claim 1 wherein the baffle is configured as a ring having a wall parallel to the axis.

3. The oven of claim 2 wherein the ring and blades have approximately the same diameter.

4. The oven of claim 1 further including means located outside of the oven for sucking air from the oven interior through the outlet means while the outlet means is open.

5. The oven of claim 4 wherein the sucking means includes further fan blades.

6. The oven of claim 4 wherein the sucking means includes further fan blades located in a low pressure cavity separated from the inlet means by a further baffle.

7. The oven of claim 6 wherein the further baffle has an opening so air is sucked through it into the cavity by the further fan blades while the inlet and outlet means are closed.

8. The oven of claim 7 further including a housing around the oven, the housing including a tortuous path having opening means through which ambient air is introduced, air in the tortuous path being drawn over the oven exterior and through the opening in the further baffle by the further fan blades and being drawn over the oven exterior and through the inlet means by the blades while the inlet and outlet means are open.

9. The oven of claim 1 wherein the inlet means is positioned so substantially all air sucked by the blades flows into the oven interior by way of the interior of the baffle, and the outlet means is positioned so substantially all air flowing through it flows outside of the baffle.

10. An oven and housing for heating chromatography columns mounted therein and for enabling the columns to be cooled quickly, comprising:

an oven enclosure having a wall, the oven having an interior in which is located only the following elements with significant thermal mass:

mounting means for the columns, a fan assembly having a shaft carrying blades, said fan assembly being centrally mounted with respect to the wall, and said shaft extending through the geometric center of the wall to the exterior of said oven where said shaft is driven by motor means exterior to said oven, a heater located coaxially with said shaft betweean the blades and the wall, a baffle surrounding the heater located coaxially with the shaft and the heater between the blades and the wall, the baffle, heater and blades being configured and located in the oven so that the fan functions as a mixed circumferential and axial fan whereby air directed by the blades is incident on the columns without first being intercepted by walls of the oven and the circumferentially directed air is substantially prevented by the baffle from directly reaching the heater, and whereby the small number and mass of the elements within the oven causes the oven to have a relatively low thermal mass, and selectively opened and closed air inlet and outlet means on the wall, the inlet and outlet means being located so that when the inlet and outlet means are opened, air at approximately ambient temperature and pressure is drawn by the blades through the inlet means into the oven enclosure to cool the columns and so that air does not flow direcly to the outlet means; and a housing surrounding said oven, said housing comprising:

a second fan assembly located in a low pressure cavity separated from said inlet means by a second baffle, said fan being configured to suck air from the oven interior through said outlet means when said outlet means is open and said second baffle having an opening such that air is sucked through the opening in said second baffle into the low pressure cavity when said inlet and outlet means are closed, and a tortuous path having opening means through which ambient air is introduced, said air in the tortuous path being drawn over the exterior walls of the oven and through the opening in said second baffle by said second fan assembly and being drawn over the exterior walls of the oven and through the inlet means by the blades when the inlet and outlet means are opened.

11. The oven of claim 10 wherein the housing includes: a closed compartment for fluid flow controllers for the columns, an additional baffle between the closed compartment and the oven, the opening means supplying ambient air to both sides of the additional baffle so air flowing on one side of the additional baffle flows about the closed compartment and has a substantial effect on the closed compartment temperature and air flowing on the other side of the additional baffle flows in the tortuous path.

12. The oven of claim 11 wherein the additional baffle includes an opening positioned downstream of the closed compartment so air from the one side of the additional baffle is sucked through the opening in the additional baffle by at least one of the further fan blades and the blades in the oven.

13. An oven for heating chromatography columns mounted therein and for enabling the columns mounted in the oven to be cooled relatively quickly comprising an oven enclosure having a wall, the oven having an interior in which is located mounting means for the columns, a fan having blades in the enclosure, a heater located between the wall and the blades, a baffle surrounding the heater and located between the wall and the blades, the baffle, heater and blades being configured and located in the enclosure so that the fan functions as a mixed circumferential and axial fan whereby air directed by the blades is incident on the columns without first being intercepted by walls of the oven and the circumferentially directed air is substantially prevented by the baffle from directly reaching the heater, the small number and mass of items in the enclosure causing the enclosure to have a relatively low thermal mass; and selectively opened and closed air inlet and outlet means on the wall, the inlet and outlet means being located so that when the inlet and outlet means are open air at approximately ambient temperature and pressure is drawn by the blades through the inlet means and the baffle into the enclosure to cool the columns and air drawn into the enclosure by the blades through the inlet means does not flow directly to the outlet means.

14. The oven of claim 13 wherein the baffle is configured as a ring having a wall parallel to the axis, the baffle and ring being coaxial with the blades.

15. The oven of claim 14 wherein the ring and blades have approximately the same diameter.

16. The oven of claim 13 further including means located outside of the oven for sucking air from the oven interior through the outlet means while the outlet means is open.

17. The oven of claim 16 wherein the sucking means includes further fan blades.

18. The oven of claim 16 wherein the sucking means includes further fan blades located in a cavity separated from the inlet means by a further baffle outside of the oven.

19. The oven of claim 18 wherein the further baffle has an opening for enabling air to flow through it into the cavity while the inlet and outlet means are closed.

20. The oven of claim 17 further including a housing around the oven, the housing including a tortuous path having opening means through which ambient air is introduced, air in the tortuous path being drawn over the oven exterior and through the opening in the further baffle by the further fan blades and being drawn over the oven exterior and through the inlet means by the blades while the inlet and outlet means are open.

21. The oven of claim 13 wherein the inlet means is positioned so substantially all air sucked by the oven blades flows into the oven interior by flowing through the interior of the baffle, and the outlet means is positioned outside of the baffle at a high pressure region in the oven so the pressure at the region has a tendency to force the air at the region through the outlet means.

22. The oven of claim 21 further including means located outside of the oven for sucking air from the high pressure region through the outlet means while the outlet means is open.

23. An oven for heating chromatography columns mounted therein and for enabling the columns to be cooled quickly, comprising:

an oven enclosure having a wall, the oven having an interior in which is located only the following elements with significant thermal mass:

mountng means for the columns, a fan assembly having a shaft carrying blades, said fan assembly being centrally mounted with respect to the wall, and said shaft extending through the geometric center of the wall to the exterior of said oven where said shaft is driven by motor means exterior of said oven, a heater located coaxially with said shaft between the blades and the wall, a baffle surrounding the heater located coaxially with the shaft and the heater between the blades and the wall, the baffle, heater and blades being configured and located in the oven so that the fan functions as a mixed circumferential and axial fan whereby air directed by the blades is incident on the columns without first being intercepted by walls of the oven and the circumferentially directed air is substantially prevented by the baffle from directly reaching the heater, and whereby the small number and mass of the elements within the oven causes the oven to have a relatively low thermal mass, and selectively opened and closed air inlet and outlet means on the wall, the inlet and outlet means being located so that when the inlet and outlet means are opened, air at approximately ambient temperature and pressure is drawn by the blades through the inlet means into the oven enclosure to cool the columns and so that air does not flow directly to the outlet means, and wherein the inlet means is positioned so substantially all air sucked by the blades flows into the oven interior by way of the interior of the baffle, and the outlet means is positioned so substantially all air flowing through it flows outside of the baffle.

24. An oven and housing for heating chromatography columns mounted therein and for enabling the columns to be cooled quickly, comprising:

an oven enclosure having a wall, the wall having an interior in which is located:

mounting means for the columns, a fan having blades, a heater located between the wall and the blades, a baffle surrounding the heater and located between the wall and the blades, the baffle, heater and blades being configured and located in the oven so that the fan functions as a mixed circumferential and axial fan whereby air directed by the blades is incident on the columns without first being intercepted by walls of the oven and circumferentially directed air is substantially prevented by the baffle from directly reaching the heater, the small number and mass of items in the oven causing the oven to have a relatively low thermal mass, selectively opened and closed air inlet and outlet means on the wall, the inlet and outlet means being located so that when the inlet and outlet means are opened, air at approximately ambient temperature and pressure is drawn by the blades through the inlet means and the baffle into the oven enclosure to cool the columns and air drawn into the oven enclosure by the blades through the inlet means does not flow directly to the outlet means; and a housing around the oven enclosure, comprising:

a second fan assembly located in a cavity separated from the inlet means by a further baffle outside of the oven whereby air from the oven interior is sucked through the outlet means while the outlet means is open, and a tortuous path having opening means through which ambient air is introduced, air in the tortuous path being drawn over the oven exterior and through the opening in the further baffle by the second fan assembly and being drawn over the oven exterior and through the inlet means by the blades while the inlet and outlet means are open.

25. The oven of claim 24 wherein the housing includes: a closed compartment for fluid flow controllers for the columns, an additional baffle between the closed compartment and the oven, the opening means supplying ambient air to both sides of the additional baffle so air flowing on one side of the additional baffle flows about the closed compartment and has a substantial effect on the closed compartment temperature and air flowing on the other side of the additional baffle flows in the tortuous path.

26. The oven of claim 25 wherein the additional baffle includes an opening positioned downstream of the closed compartment so air from the one side of the additional baffle is sucked through the opening in the additional baffle by at least one of the further fan blades and the blades in the oven.

27. An oven enclosure for heating and thereafter cooling chromatography columns mounted therein, comprising within the oven enclosure:

at least one chromatography column and mounting means therefor, said mounting means being located on the walls of the oven enclosure and providing means for transmitting fluids into and out of the column through the walls of the oven enclosure to the exterior of the oven enclosure, a ring-shaped heating element mounted on a wall of said oven enclosure, a ring-shaped baffle mounted coaxially with respect to said heating element, surrounding said heating element, and having approximately the same diameter as said heating element, a fan having a shaft extending through said wall of the oven enclosure, driven by an external motor, and mounted coaxially with respect to said heating element and said baffle and outwardly therefrom in respect to said wall, said fan being positioned in respect to said baffle, said heating element and said column such that air within the oven enclosure is circulated from the fan blades directly to the column without first intercepting any other item within the oven enclosure, and selectively opened and closed inlet and outlet means located on a wall of the oven enclosure, whereby when said inlet and outlet means are open, air from the exterior of said oven enclosure is drawn through said inlet means by said fan, circulated within the oven enclosure and thereafter exhausted through said outlet means to the exterior of the oven enclosure.

28. The oven enclosure of claim 27 wherein said fan is of generally circular shape with blades extending radially from said shaft, the diameter of said fan being slightly greater than the diameter of said baffle.

29. The oven enclosure of claim 28 having a first narrow clearance between said baffle and said fan blades and a second narrow clearance between said baffle and said wall of the oven enclosure, whereby said first and second narrow clearances restrict the flow of air into the space between said fan and said wall wherein said heater is located.

30. The oven enclosure of claim 28 wherein said inlet means comprises a door in said wall, said inlet door being located in the area of the wall surrounded by said baffle and behind said fan, and wherein said outlet means comprises a door in said wall, said outlet door being located in an area of the wall radially outwardly of said baffle.

* * * * *